United States Patent
Pašek et al.

(10) Patent No.: US 6,809,222 B1
(45) Date of Patent: Oct. 26, 2004

(54) PROCESS OF PREPARATION OF ALIPHATIC AMINES

(75) Inventors: Josef Pašek, Prague (CZ); Josef Koubek, Prague (CZ); Stanislav Sandtner, Modra (SK); Ivan Dlouhý, Prague (CZ); Július Kozma, Bratislava (SK); Pavol Škubla, Šaľa (SK)

(73) Assignees: Duslo A.S., Sala (SK); Vucht, A.S., Bratislava (SK); Vysoká Škola Chemicko-Technologicá, Prague (CZ)

( * ) Notice: Subject to any disclaimer, the term of this patent is extended or adjusted under 35 U.S.C. 154(b) by 0 days.

(21) Appl. No.: 10/276,027

(22) PCT Filed: May 12, 2000

(86) PCT No.: PCT/SK00/00008

§ 371 (c)(1),
(2), (4) Date: Mar. 4, 2003

(87) PCT Pub. No.: WO01/85667

PCT Pub. Date: Nov. 15, 2001

(51) Int. Cl.$^7$ .............................................. C07C 209/60
(52) U.S. Cl. ....................................................... 564/485
(58) Field of Search ......................................... 564/485

(56) References Cited

U.S. PATENT DOCUMENTS

| | | | |
|---|---|---|---|
| 2,381,470 A | * 8/1945 | Teter .......................... | 558/330 |
| 4,307,250 A | * 12/1981 | Peterson et al. ............. | 564/445 |
| 4,375,002 A | 2/1983 | Peterson et al. ............. | 564/445 |
| 4,929,759 A | 5/1990 | Taglieber et al. ........... | 564/485 |
| 5,648,546 A | * 7/1997 | Bergfeld et al. ............. | 564/485 |

* cited by examiner

*Primary Examiner*—Brian Davis
(74) *Attorney, Agent, or Firm*—Ohlandt, Greeley, Ruggiero & Perle, LLP; George W. Rauchfuss, Jr.

(57) ABSTRACT

Aliphatic amines are obtained by continuous addition of ammonia to $C_2$- to $C_8$-alkenes in the presence of a heterogeneous or homogeneous catalyst at a pressure of 2 to 8 MPa, a temperature of 220 to 320° C. and a molar ratio of ammonia to the alkene of 1.5 to 20, while the gaseous reaction mixture which leaves the second section, is cooled to a temperature near the dew point, it is led to the enrichment part of the first section, where it is sprayed in counterflow with a liquid mixture consisting of the starting substances. The unreacted starting substances thus disposed of the most of the amine formed are recycled under pressure in gaseous state to the second section, the liquid mixture in the impoverishment part of the section gets rid of the unreacted starting substances, and from the bottom of the first section the concentrate is conducted to further processing.

9 Claims, No Drawings

PROCESS OF PREPARATION OF ALIPHATIC AMINES

This application is a 371 of PCT/SK00/00008 filed May 12, 2000.

TECHNICAL FIELD

Present invention is concerned with a process of preparation of aliphatic amines by ammonia addition to alkenes.

BACKGROUND ART

Most of aliphatic amines are produced by amination of alcohols or possibly by amination of carbonyl compounds. Only currently the addition of ammonia to alkenes starts to be applied according to the scheme

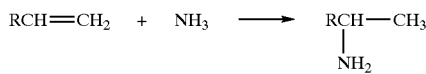

The reaction is exothermic, while the equilibrium constant decreases with increasing temperature. Therefore, active catalysts are sought which would provide for sufficient reaction rate also at a temperature of 200 to 250° C. at which the equilibrium conversion of an alkene to an amine is more favourable.

Of course, increasing pressure improves the equilibrium conversion of an alkene to an amine, and most of the current publications and patents give a pressure higher than 2 MPa, and in several cases even 70 MPa.

The reaction rate depends on the catalyst activity, but also on the alkene reactivity. Isobutene is highly reactive, propene reacts more slowly, and ethylene has the smallest activity. While isobutylene reacts with ammonia on a zeolite catalyst quickly enough already at a temperature of 250° C., ethylene requires a temperature of about 350° C.

Many substances have been tried as homogeneous and heterogeneous catalysts for the ammonia addition to alkenes. The greatest attention has been paid to zeolite type catalysts. From U.S. Pat. Nos. 4,307,250 and 4,375,002 Y- and X-type zeolites, including various modifications, are known as catalysts which work at the following conditions:

| | |
|---|---|
| pressure | 2.06 to 41.3 MPa |
| temperature | 200 to 450° C. |
| molar ratio $NH_3$/alkene | 0.2 to 20. |

With H-mordenite as a catalyst at a temperature of 300 to 320° C., a pressure of 5 MPa and a molar ratio $NH_3$/isobutene of 3.95 isobutylene conversion of 15 to 26% was reached in single experiments, but the conversion selectivity to tert-butylamine was relatively low, reaching 24 to 72%. In the above mentioned patent documents the side products have not been described, and they are probably oligomers of isobutylene. In EP 0305 564 A1 there is described a partially dealuminized zeolite catalyst which has a higher activity and selectivity, leading to a conversion of 3.8 to 13.6% at a temperature of 220 to 260° C., a pressure of 5 MPa and at a molar ratio $NH_3$/isobutylene=4.

In DE 33 26 579 A1 there is described a method of amine preparation by alkene amination in the presence of a pentasil-type catalyst. An advantage of this catalyst in comparison with the Y-type is higher selectivity and lower formation of carbonaceous deposits, namely at a relatively small excess of ammonia. The pressure of 30 MPa is considered to be optimal, and the highest isobutylene conversion of 12% has been reached at a temperature of 330° C., a pressure of 59 MPa and at a molar ratio $NH_3$/isobutylene=1.5. When aminating isobutylene by the method according to DE 33 27 000 A1 on a boralite-based catalyst at a molar ratio $NH_3$/isobutylene=1.5, a temperature of 300° C. and a pressure of 30 MPa an isobutylene conversion of 17.3% has been achieved.

The use of alkali metals and of their hydrides as catalysts for ammonia addition to alkenes is described in U.S. Pat. No. 2,501,556, where pressures of at least 50 MPa and a temperature of 100 to 250° C. are recommended. The use of rare metals of the group VIII, especially of palladium on a carrier, as catalysts of alkene amination is known from U.S. Pat. No. 3,412,158. The use of homogeneous catalysts, based on the solutions of ruthenium and iron complexes, in preparation of aliphatic and aromatic amines by ammonia addition to olefines at a temperature of 100 to 250° C. and a pressure of 0.1 to 83 MPa is described in EP 0039 061 B1, but the results of experiments have been evaluated only quantitatively. The use of ammonium halides as catalysts for the above mentioned reaction is known from EP 0200 923 A2, and that of organic cation exchangers from U.S. Pat. No. 4,536,602. Nevertheless, only thermostable types based on fluorine compounds are suitable. It seams that other types of catalysts of ammonia addition to olefins cannot compete with zeolites. Zeolites have excellent thermal stability and they are easily regenerated with air at a temperature of 400 to 500° C. Some of the homogeneous catalysts show corrosive action, whereas zeolites are practically inert.

Most of the patent literature which concerns the amine preparation by zeolite catalyzed addition of ammonia to olefins recommends to perform the above mentioned reaction at a relatively high pressure. For example, in DE 33 26 579 A1 and DE 33 27 000 A1 a pressure in the range of 4 to 70 MPa is considered, but a pressure of 20 to 30 MPa is recommended. Using a lower pressure, for example 5 MPa (U.S. Pat. Nos. 4,307,250, 4,375,002, EP 0305 564 A1), the alkene conversion to amine of about 10% is achieved only with a high excess of ammonia. The reaction mixture is liquefied by cooling, and the unreacted starting substances are separated by rectification. If a higher ammonia excess is used, even more than 10 kg of ammonia, which has high heat of vaporization, per 1 kg of the prepared amine must be evaporated. At a pressure of 30 MPa a similar isobutylene conversion can be achieved also at a molar ratio $NH_3$/isobutylene of 1.5. However, a high-pressure apparatus is very expensive, and injecting the liquids into a high pressure requires much energy for driving the injection pumps.

DISCLOSURE OF INVENTION

At present it has been found that it is possible to produce aliphatic amines by the ammonia addition to alkenes using a method according to the present invention which eliminates the high heat consumption of the known procedures. The nature of the method of preparation of aliphatic amines from ammonia and alkenes in the gas phase using homogeneous or heterogeneous catalysts consists in that the reaction system consists of two sections which are mutually interconnected and conditioned and of one cooling zone which work at a practically equal pressure of 2 to 8 MPa, while the starting ammonia and alkene enter the first section, where they are mixed with the unreacted ammonia and alkene at the pressure of the synthesis, and the gaseous mixture enters the second section, where a partial chemical transformation of reactants to amine takes place, and the reaction mixture leaving the second section passes the cooling zone and returns to the first section, where the separation of the gaseous mixture of unreacted ammonia and alkenes from the liquid crude amine takes place, which crude amine is further purified.

Synthesis of amines from alkenes and ammonia in the system of two mutually conditioned sections working at a practically equal pressure according to the present invention allows that it can be only performed in a relatively narrow range of pressures of 2 to 8 MPa. The term "practically equal pressure" means that the pressure differences in the sections are caused only by the pressure loss in the apparatus and pipes. The upper bound for the working pressure is given by the closeness of the critical pressure of ammonia or of its mixture with an alkene. The function of the first section is namely conditioned by simultaneous existence of the gaseous and liquid phase in it. The critical pressure for ammonia is 11.2 MPa, the critical pressure, for example, for isobutylene is 4.0 MPa.

Only a small part of amines can be separated by a simple partial condensation in the first section at the system pressure. The amine content in the mixture which leaves the second (catalytic) section is namely limited by equilibrium, and it represents only 1 to 3 molar % of the amine. Conversion of alkenes to amine under the conditions according to the invention is 3 to 10%, and the amine content is further decreased by the excess of ammonia. Therefore, according to the present invention the efficiency of the amine separation from the gaseous mixture is preferably increased by a built-in packing which increases the surface of the interfacial contact of the gas and liquid, while the gas and liquid counterflowly pass the first section. A suitable built-in packing is formed by valve, bubble-cap or sieve trays; orientated or non orientated fillings have small efficiency at a pressure near the critical pressure.

The counterflow of the gas and liquid in the first section can be ensured by partial condensation of the unreacted part of the starting mixture of alkene and ammonia in the upper part of the first section, possibly also by feeding with fresh liquid reactants at the top of the first section. A suitable separation efficiency, expressed as a number of gas-liquid equilibrium (theoretical) plates, is 10 to 30.

The second section of the reaction system contains any catalyst which accelerates the ammonia addition to the alkene at a pressure which is conditioned by the function of the first section, i.e. 2 to 8 MPa. The reaction temperature alone doesn't constitute any invention condition, but it must be such that it, together with a given catalyst, provides for practically applicable rate of amine forming. The lower bound of the temperature of 220° C. is limited by kinetics, the upper bound 320° C. is limited by achievable equilibrium conversion under the system pressure. A further condition for the selection of a temperature is the gaseous form of the mixture which leaves the second section.

A relatively great amount of gaseous reactants are circulated through the reaction system, while from the bottom of the first section liquid crude amine is withdrawn which is then purified by a common method. The crude amine contains a certain amount of starting substances, i.e. alkenes and ammonia. Circulation of the gaseous mixture through the sections is ensured by a suitable compressing machine which is able to work at a temperature of 80 to 120° C. At a lower temperature the reactants would have condensated. Noting that the pressure loss in both sections and in the cooling zone is usually only 3 to 10%, when referred to the pressure of the synthesis, the energy consumption for the reactant circulation is very low. At usual conditions of the amine synthesis from alkenes and ammonia at a pressure of 20 to 30 MPa a higher conversion of the alkene can be obtained, but the liquid reaction mixture must be rectified in a separate line, and isolated starting substances are recycled in the liquid phase. The reactants are thus evaporated twice, at first in rectifying columns, then before entering the reactor. On the other hand the heat consumption at the bottom of the first section of the amine synthesis according to the present invention is very low, and the energy consumption for the inner circulation of gaseous reactants is also low. The energy costs in the synthesis according to the present invention are about a half of those for common procedures. Due to low energy consumption in the amine synthesis according to the present invention it is possible to work also with very low conversion of alkenes in the second section which is important for the amination of less reactive alkenes, like propylene and ethylene.

The equipment for the operation at a pressure of 2 to 8 MPa is considerably cheaper than an equipment for common amine synthesis at a pressure of 20 to 30 MPa.

Molar ratio $NH_3$/alkene which is determined by the alkene type plays a certain role in the amine synthesis according to the present invention. The higher the boiling point of the alkene, the higher molar ratio must be used. With increasing ammonia excess the equilibrium conversion of alkenes to amine is increasing on one hand, on the other hand the amount of reactants which circulate through the system of the first and second section is increased. If acidic heterogeneous catalysts are applied, strong sorption of ammonia decreases the addition rate. For example, if isobutylene is reacted to tert-butylamine using the zeolites ZSM-5 in the second section of the system and at a pressure of 4 MPa, the amine formation rate at a molar ratio $NH_3$/isobutylene=4 is 30% less than that at the molar ratio of 2. When the method according to the present invention is used, the optimum molar ratio $NH_3$/isobutylene at the entry into the second section lies just in the range of 2 to 4.

A high ammonia excess is necessary in the addition of ammonia to alkenes which boil at higher temperatures. For example, when producing cyclohexylamine from cyclohexene it is possible to circulate the gaseous reactants from the first to the second section at a pressure of 3 MPa only at a molar ratio of 15 to 20.

EXAMPLES OF EMBODIMENTS

Example 1

The upper part of the first section is fed with a fresh mixture of isobutylene and ammonia using a pump, which mixture is, together with the condensate which runs off the dephlegmator, mixed in the central part of the first section with the reaction mixture, cooled to a temperature of 120° C., which is incoming from the first section. The second section is provided with a built-in packing having the efficiency of 15 equilibrium (theoretical) plates which is, together with the overall reflux ratio of 0.35, sufficient for separation of 95% of tert-butylamine from the mixture. The gases which leave the dephlegmator have a temperature of 90° C., they are heated to 100° C., and they are transported by means of a membrane compressor through a preheater to the second section which is filled with two liters of the ZSM-5-type zeolite catalyst in the form of compacts, where they react to tert-butylamine at a temperature of 250° C. and a pressure of 3.9 MPa. The conversion of isobutylene to tert-butylamine is 5% and the selectivity is 99.5%. The first section is fed with such an amount of fresh ammonia and isobutylene that 70 moles of isobutylene and 210 moles of ammonia per hour enter the second section. From the bottom of the first section which is heated to 165° C. liquid mixture is leaving which contains 50% of tert-butylamine, approximately the same amount of isobutylene and only 0.02% of isobutylene dimers.

Example 2

Using the same equipment as in Example 1, synthesis of 2-aminopropane from propylene and ammonia was performed at a temperature of 320° C. and a pressure of 5 MPa. Using a molar ratio $NH_3$/propylene of 4 the conversion of alkenes to amine was 3%. The first section of the synthesis system has worked at a reflux ratio of 0.25, ensuring separation of 95% of amine, contained in the mixture incoming from the second section. In the upper part of the first section there was a temperature of 95° C., bottom of the first section was heated to 134° C. From the bottom of the first section crude 2-aminopropane, containing 7% by weight of ammonia and 18% by weight of propylene, has been withdrawn.

What is claimed is:

1. A process for the production of aliphatic amines by ammonia addition to alkenes in gaseous phase, catalyzed by homogeneous or heterogeneous catalysts, wherein the process is conducted in a synthesis system comprising two sections, a first reactive section and a second separative section which are mutually interconnected and dependent, and of one cooling zone working at practically the same pressure of from about 2 to about 8 MPa, and wherein the first reactive section contains a catalyst and the second separative section is equipped with built-in packing for intensification of mutual counterflow contact of liquid and gaseous phases, and wherein the process comprises permitting ammonia and alkene to enter into the reactive section containing catalyst and permitting the alkene to partially react with ammonia to form amine, permitting the reactive mixture to leave the reactive section and enter the cooling zone, and after being cooled in the cooling zone to enter the separative section where amine concentrate is separated from the reactive mixture, and amine concentrate is permitted to leave a heated bottom portion of the separative section, and this amine concentrate is then permitted to be further refined, and unreacted mixture of alkenes and ammonia is recycled in gaseous form from a condenser in this section back into the reactive section along with fresh ammonia and alkene reactants.

2. A process according to claim 1, wherein the number of carbon atoms in the alkene is 2 to 8.

3. A method according to claim 2, wherein the alkene is isobutylene.

4. A method according to claim 1, wherein the catalyst in the reactive section is a heterogeneous zeolite catalyst.

5. A method according to claim 1, wherein the catalyst in the reactive section is a zeolite catalyst of the ZSM-5-type.

6. A method according to claim 1, wherein a temperature of 220 to 320° C. is kept in the reactive section.

7. A method according to claim 1, wherein a molar ratio of ammonia to alkene at the entry into the reactive section is 1.5 to 20.

8. A method according to claim 1, wherein the reaction mixture is cooled in the cooling zone to a temperature near the dew point.

9. A method according to claim 1, wherein the reaction mixture is cooled in the cooling zone to a temperature near the dew point by means of a heat exchange with the mixture which has been recycled from the separative section to the reactive section.

* * * * *